United States Patent
Marshall

(10) Patent No.: US 10,867,700 B2
(45) Date of Patent: Dec. 15, 2020

(54) ELECTRONIC WELLNESS CHECK FOR ESTABLISHING MEDICAL STAFF INTEGRITY AND HIGH FUNCTIONAL EFFICIENCY

(71) Applicant: Theresa R. Marshall, Longmeadow, MA (US)

(72) Inventor: Theresa R. Marshall, Longmeadow, MA (US)

( * ) Notice: Subject to any disclaimer, the term of this patent is extended or adjusted under 35 U.S.C. 154(b) by 290 days.

(21) Appl. No.: 15/640,996

(22) Filed: Jul. 3, 2017

(65) Prior Publication Data

US 2018/0018435 A1    Jan. 18, 2018

Related U.S. Application Data

(60) Provisional application No. 62/363,773, filed on Jul. 18, 2016.

(51) Int. Cl.
*G16H 40/20* (2018.01)
*G16H 10/60* (2018.01)
(Continued)

(52) U.S. Cl.
CPC ......... *G16H 40/20* (2018.01); *G06F 21/6245* (2013.01); *G16H 10/60* (2018.01);
(Continued)

(58) Field of Classification Search
CPC ........ G16H 40/20; G16H 40/67; G16H 10/60; G16H 50/20; G06F 21/6245;
(Continued)

(56) References Cited

U.S. PATENT DOCUMENTS 7,389,928 B2 * 6/2008 Lubow ................... G06K 17/00
                                                         235/462.01
8,766,789 B2 * 7/2014 Cosentino ........... G06F 19/3418
                                                          340/539.12
(Continued)

OTHER PUBLICATIONS

Safinofsky, Isaac, Preventing Suicide Among Inpatients, CanJPsychiatry 2014; 59(3):131-140 (Year: 2014).*

*Primary Examiner* — Jonathan Durant
*Assistant Examiner* — Anne-Marie K Alderson
(74) *Attorney, Agent, or Firm* — Zilka-Kotab, P.C.

(57) ABSTRACT

A device-implemented method according to one embodiment includes connecting a device to a medical record library system; receiving a valid user access credential; in response to receiving the valid user credential, granting selective user access to the device; receiving a selection of a patient profile corresponding to a patient; receiving location data of the patient corresponding to the selected patient profile; outputting, to a display of the device, a graphical representation of the location of the patient based on the location data; determining whether the device is within a predetermined proximity of the patient; allowing receipt of wellness data of the patient in response to a determination that the device is within the predetermined proximity of the patient; denying receipt of the wellness data in response to a determination that the device is not within the predetermined proximity; and updating the selected patient profile with the location and wellness data.

20 Claims, 4 Drawing Sheets

(51) Int. Cl.
  *G16H 50/20* (2018.01)
  *G16H 40/67* (2018.01)
  *G06F 21/62* (2013.01)
  *H04L 29/06* (2006.01)
(52) U.S. Cl.
  CPC ............ *G16H 40/67* (2018.01); *G16H 50/20* (2018.01); *H04L 63/083* (2013.01); *H04L 63/0861* (2013.01); *H04L 63/102* (2013.01); *H04L 63/107* (2013.01)
(58) Field of Classification Search
  CPC . H04L 63/083; H04L 63/0861; H04L 63/102; H04L 63/107
  See application file for complete search history.

(56) References Cited

U.S. PATENT DOCUMENTS

| | | | | |
|---|---|---|---|---|
| 8,890,685 | B1* | 11/2014 | Sookman | G08B 25/008 340/539.13 |
| 9,805,573 | B2* | 10/2017 | Herbst | G16H 10/60 |
| 9,872,641 | B2* | 1/2018 | Sloan | G16H 10/40 |
| 10,164,985 | B2* | 12/2018 | Turgeman | H04L 63/102 |
| 2003/0227386 | A1* | 12/2003 | Pulkkinen | A61B 5/1113 340/573.1 |
| 2009/0205022 | A1* | 8/2009 | Sanchez | H04L 63/064 726/4 |
| 2011/0001605 | A1* | 1/2011 | Kiani | G16H 40/20 340/5.6 |
| 2012/0075060 | A1* | 3/2012 | Connor | G16H 40/20 340/5.54 |
| 2013/0218583 | A1* | 8/2013 | Marcolongo | G06F 19/3418 705/2 |
| 2014/0142979 | A1* | 5/2014 | Mitsunaga | G16H 10/60 705/3 |
| 2014/0189808 | A1* | 7/2014 | Mahaffey | H04L 63/083 726/4 |
| 2015/0227127 | A1* | 8/2015 | Miller | G05B 19/042 700/244 |
| 2016/0246472 | A1* | 8/2016 | Zhao | G06F 1/1694 |
| 2016/0253470 | A1* | 9/2016 | Marcolongo | G06F 19/3418 705/2 |
| 2017/0228508 | A1* | 8/2017 | Cook | H04W 4/023 |

* cited by examiner

ELECTRONIC WELLNESS CHECK FOR ESTABLISHING MEDICAL STAFF INTEGRITY AND HIGH FUNCTIONAL EFFICIENCY

RELATED APPLICATIONS

This application claims priority to U.S. Provisional Patent Appl. No. 62/363,773, filed on Jul. 18, 2016 and entitled "Medical Electronic Checks Tablet" and which is herein incorporated by reference.

FIELD OF THE INVENTION

The present invention relates to wellness recording practices at medical facilities, and more particularly, this invention relates to the obtaining and recording of patient wellness data.

BACKGROUND

Medical facilities that host patients often implement reoccurring care practices that are performed throughout a patient's admittance. Where desirable, some of such practices includes, e.g., administering medicines to patients, collecting health data of patients, etc. This practice is commonly referred to as "rounds."

Rounds are often performed by medical staff members, such as nurses and/or doctors. To document the wellness of patients, while performing rounds, staff members often record data that corresponds to the patient's wellness during a particular round checkup. Conventional methods of recording such data includes physically writing the patient data into a data spreadsheet. This data is compiled in a patient's medical records for future reference.

Rounds are often implemented in psychiatric care facilities, as psychiatric units many times require ongoing and scheduled observation. Rounds are also implemented in Intensive Care Units (ICUs) or Medical Units, where a patient's life is often saved in response to frequent scheduled rounds being performed on the suffering patient.

SUMMARY

A device-implemented method for performing a patient wellness check according to one embodiment includes connecting a device to a medical record library system; receiving, by the device, a valid user access credential; in response to receiving the valid user access credential, granting, by the device, selective user access to the device; receiving, by the device, a selection of a patient profile corresponding to a patient; receiving, by the device, location data of the patient corresponding to the selected patient profile; outputting, to a display of the device, a graphical representation of the location of the patient based on the location data; determining whether the device is within a predetermined proximity of the patient; allowing, by the device, receipt of wellness data of the patient in response to a determination that the device is within the predetermined proximity of the patient; denying receipt of the wellness data in response to a determination that the device is not within the predetermined proximity of the patient; and updating, using the device, the selected patient profile with the location and wellness data. The location data includes at least a most recent location of the patient of the selected patient profile. The wellness data includes at least measured health data and observational data of the patient, input by a user of the device. The updated patient profile includes a first time stamp, the first time stamp corresponding to a time the wellness data was received.

A computer program product for performing a patient wellness check according to another embodiment includes a computer readable storage medium having program code stored thereon. The program code is executable by a device to cause the device to perform a process including connecting, by the device, to a medical record library system; receiving, by the device, a valid user access credential; in response to receiving the valid user access credential, granting, by the device, selective user access to the device; receiving, by the device, a selection of a patient profile corresponding to a patient; receiving, by the device, location data of the patient corresponding to the selected patient profile; outputting, to a display of the device, a graphical representation of the location of the patient in response based on the location data; determining, by the device, whether the device is within a predetermined proximity of the patient; allowing, by the device, receipt of wellness data of the patient in response to a determination that the device is within the predetermined proximity of the patient; denying, by the device, receipt of the wellness data in response to a determination that the device is not within the predetermined proximity of the patient; and updating, using the device, the selected patient profile with the location and wellness data. The location data includes at least a most recent location of the patient of the selected patient profile. The wellness data includes at least measured health data and observational data of the patient, input by a user of the device. The updated patient profile includes a first time stamp, the first time stamp corresponding to a time the wellness data was received.

Other aspects and advantages of the present invention will become apparent from the following detailed description, which, when taken in conjunction with the drawings, illustrate by way of example the principles of the invention.

DETAILED DESCRIPTION

Figure 1:
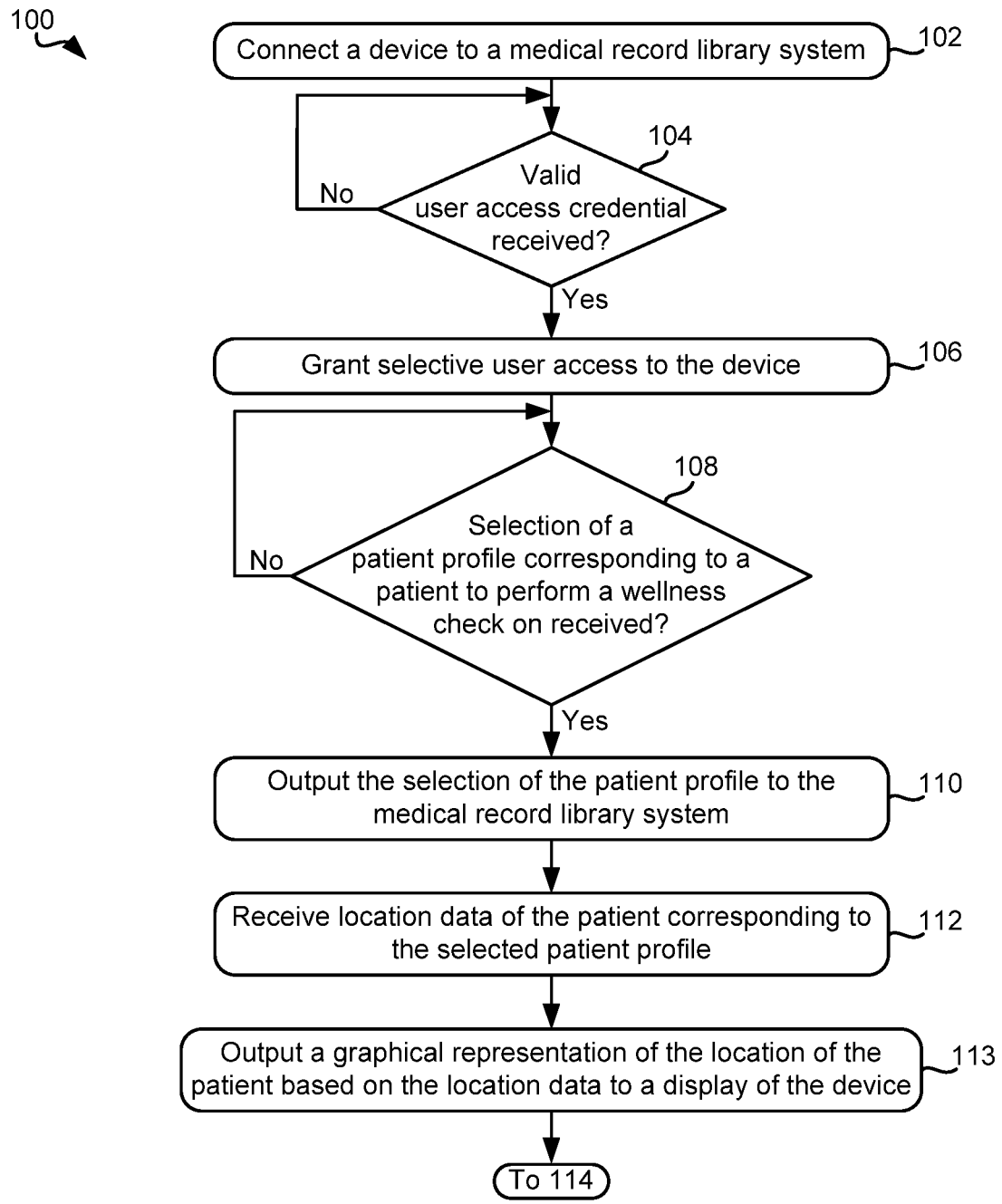
FIG. 1 is a flowchart of a method, in accordance with one embodiment.
Figure 1:
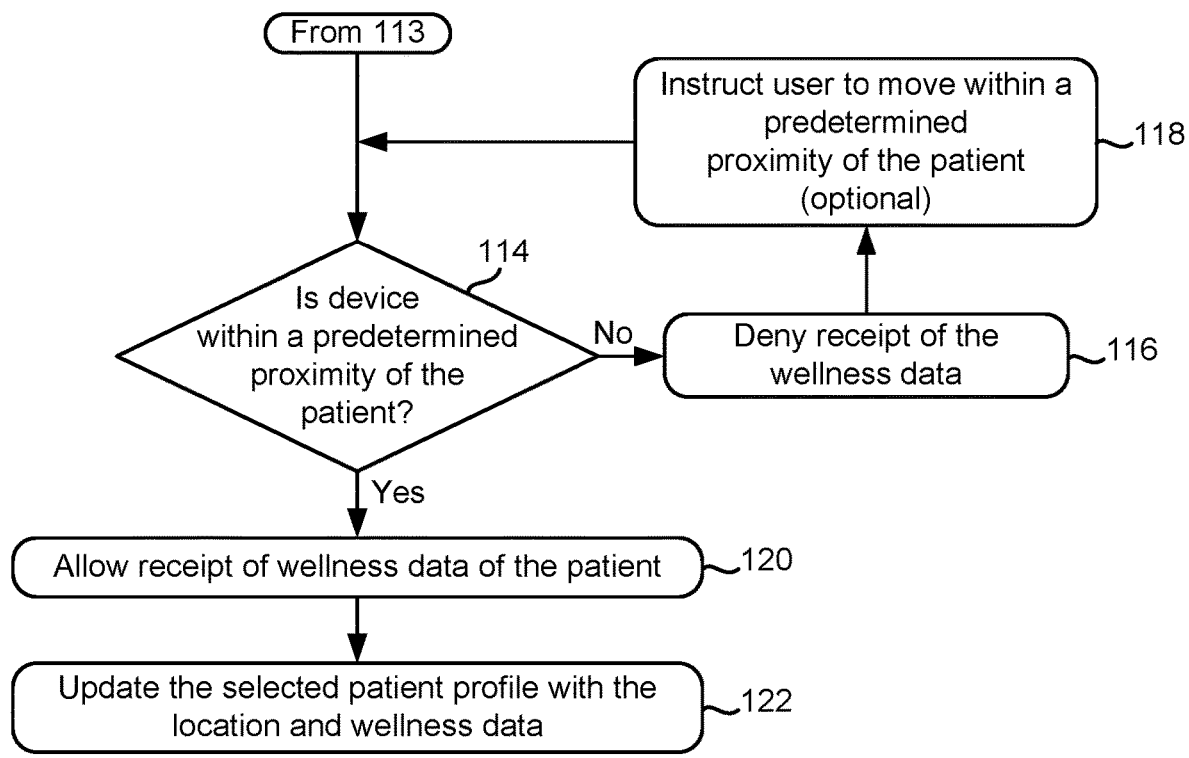

The following description is made for the purpose of illustrating the general principles of the present invention and is not meant to limit the inventive concepts claimed herein. Further, particular features described herein can be used in combination with other described features in each of the various possible combinations and permutations.

Unless otherwise specifically defined herein, all terms are to be given their broadest possible interpretation including meanings implied from the specification as well as meanings understood by those skilled in the art and/or as defined in dictionaries, treatises, etc.

It must also be noted that, as used in the specification and the appended claims, the singular forms "a," "an" and "the" include plural referents unless otherwise specified.

The following description discloses several preferred embodiments of performing patient wellness checks and/or related systems and methods.

In one general embodiment, a device-implemented method for performing a patient wellness check includes connecting a device to a medical record library system; receiving, by the device, a valid user access credential; in response to receiving the valid user access credential, granting, by the device, selective user access to the device; receiving, by the device, a selection of a patient profile corresponding to a patient; receiving, by the device, location data of the patient corresponding to the selected patient profile; outputting, to a display of the device, a graphical representation of the location of the patient based on the location data; determining whether the device is within a predetermined proximity of the patient; allowing, by the device, receipt of wellness data of the patient in response to a determination that the device is within the predetermined proximity of the patient; denying receipt of the wellness data in response to a determination that the device is not within the predetermined proximity of the patient; and updating, using the device, the selected patient profile with the location and wellness data. The location data includes at least a most recent location of the patient of the selected patient profile. The wellness data includes at least measured health data and observational data of the patient, input by a user of the device. The updated patient profile includes a first time stamp, the first time stamp corresponding to a time the wellness data was received.

In another general embodiment, a computer program product for performing a patient wellness check includes a computer readable storage medium having program code stored thereon. The program code is executable by a device to cause the device to perform a process including connecting, by the device, to a medical record library system; receiving, by the device, a valid user access credential; in response to receiving the valid user access credential, granting, by the device, selective user access to the device; receiving, by the device, a selection of a patient profile corresponding to a patient; receiving, by the device, location data of the patient corresponding to the selected patient profile; outputting, to a display of the device, a graphical representation of the location of the patient in response based on the location data; determining, by the device, whether the device is within a predetermined proximity of the patient; allowing, by the device, receipt of wellness data of the patient in response to a determination that the device is within the predetermined proximity of the patient; denying, by the device, receipt of the wellness data in response to a determination that the device is not within the predetermined proximity of the patient; and updating, using the device, the selected patient profile with the location and wellness data. The location data includes at least a most recent location of the patient of the selected patient profile. The wellness data includes at least measured health data and observational data of the patient, input by a user of the device. The updated patient profile includes a first time stamp, the first time stamp corresponding to a time the wellness data was received.

Medical facilities such as hospitals, psychiatric care facilities, intensive care trauma centers, etc., that implement round checks often instruct that such checks be performed by medical staff members, e.g., such as nurses, specialists, doctors, etc. During round checks, staff members often record patient health data during and/or subsequent to the round check. Conventional methods of recording health data includes writing the patient data into a physical spreadsheet, such as a paper spreadsheet printout. Such physical paper spreadsheets often include the option for staff members to self-document the time and location of a round check for a particular patient. For example, such an entry may include the staff member attesting to where they physically were within the medical facility, and then the location of the patient. For example the staff member may record that the patient is in bed (IB), and the staff member has the option to write or circle the time during which they were supposedly performing the wellness check. This is usually done by writing or circling a designated time sets on the paper printout.

Medical facilities have a tendency to become over admitted and/or understaffed. Staff members frequently struggle to maintain timeliness and completion of scheduled rounds and sometimes miss performing a scheduled check on a patient. This sometimes leads to the declining health of a patient where the health of the patient goes unnoticed and/or undocumented for at least some portion of time.

In some cases, to avoid being disciplined for failure to perform a scheduled round check, staff members may even create false data for a round check that the staff member did not actually perform. To do so, staff members may simply write false data into a patient's data spreadsheet. This may include a false time stamp or documenting that the patient was checked on, when the staff member never actually did so. In situations where medical staff enter false data, supervising medical staff members and/or doctors who review the data on the recording spreadsheets have no way of knowing that the data was dishonestly generated by the staff member assigned to perform the round check.

In other cases, staff members may accidentally enter data incorrectly into patient spreadsheet slots during and/or after a round check. For example, a staff member may accidently enter patient health data into an incorrect time slot. In another example, staff members may accidently enter one patient's data into a different patient's printout spreadsheet column. This is very dangerous and could lead to medical malpractice and/or patient neglect.

Embodiments described herein include methods, computer program products and systems for performing and electronically documenting wellness checks on patients. Such methods, computer program products and systems functionally streamline patient wellness checks, and hold staff members performing the checks accountable through documentation.

FIG. 1 shows a method 100 for performing a patient's wellness check, in accordance with one embodiment. As an option, the present method 100 may be implemented in devices such as those shown in the other FIGS. described herein. Of course, however, this method 100 and others presented herein may be used to form structures for a wide variety of devices and/or purposes, provide applications which may or may not be related to the illustrative embodiments listed herein. Further, the methods presented herein may be carried out in any desired environment. Moreover, more or less operations than those shown in FIG. 100 may be included in method 100, according to various embodiments. It should also be noted that any of the aforementioned features may be used in any of the embodiments described in accordance with the various methods.

Operation 102 of method 100 includes connecting a device to a medical record library system. According to various embodiments, the device may include any type of electronic device that is configured to receive user input data during a wellness check. According to one embodiment, the device may include a tablet-type device. According to another embodiment, the device may include a computer. According to yet another embodiment, the device may include a cellular device.

According to various embodiments, the connection between the system and the device may include any connection type that would be appreciated by one skilled in the art upon reading the present descriptions. According to one approach, the connection type may include an internet-type connection in which the device and server communicate wirelessly. According to another approach, the connection type may include a Bluetooth-type connection. According to another approach, the connection type may include a global positioning system (GPS) connection, e.g., using a satellite. According to another approach, the connection type may include a wireless radio-frequency identification device (RFID) connection. According to another approach, the connection type may include a plugin-type connection, in which the device is connected to the system via an initial physical (hardwired) connection with the device.

Connecting the device to the medical record library system may establish a handshake between the device and the medical record library system, e.g., for later communication between the device and system such as in operations 104-122. It should be noted that although an initial connection may connect the device to the medical record library system, according to various embodiments, the device may be re-connected, one or more times, to the medical record library system in response to the initial connection between the device to the medical record library system ending.

The connection of the device to the medical record library system may enable a user that is using the device during a wellness check to receive and/or update one or more patient medical records, as will be described elsewhere herein, e.g., see operations 112-122.

According to various embodiments, access to applications of the device may be selectively controlled by a login interface, e.g., presented to a user of the device on a display of the device. Decision 104 of method 100 includes determining if a valid user access credential has been received, e.g., received by the device.

The access credential may include any type of access credential, and may vary depending on the embodiment. Moreover, the access credential may include any combination of access credentials in embodiments which include more than one user access credential. According to one approach, the access credential may include a user password. According to another approach, the access credential may include a user username. According to yet another approach, the access credential may include facial recognition of a user. According to another approach, the access credential may include a user fingerprint scan. In such an approach the device may recognize any pre-recorded fingerprint of any one or more users. According to another approach, the access credential may include one or more user-specific security questions.

According to another approach, the access credential may include a staff-specific known security question. According to another approach, the access credential may include a cursor pattern. In such an approach, the cursor pattern may be scribed by a user on a touchpad and/or display interface of the device. According to another approach, the access credential may include an audio sampling.

The access credential may additionally and/or alternatively include a tap in-tap out selection. In such a selection a user may select entry into the device via tapping a predetermined selection portion of the device display and/or a button of the device.

In response to a valid user access credential not being received, e.g., as illustrated by the "No" logic leading from decision 104, selective user access to the device may be denied. According to one embodiment, in response to an invalid user access credential being entered into the device a predetermined number of times within a predetermined amount of time, the device may timeout the login interface for a predetermined amount of time. According to another embodiment, in response to an invalid user access credential being entered into the device a predetermined number of times within a predetermined amount of time, the device may output a notice of the repeated unsuccessful entry into the device, e.g., output to a manager of a system that includes the user device.

In response to a valid user access credential being received, e.g., as illustrated by the "Yes" logic leading from decision 104, selective user access to the device may be granted, e.g., see operation 106.

According to various embodiments, the type and extent of access to applications/data on the device may vary depending on the user logging into the device. In such embodiments, a particular and/or pre-set type and extent of access to applications/data on the device may be granted to a particular user in response to receiving the particular user's valid user access credential. For example, according to one approach, in response to receiving the valid user credentials of a user that is a nurse, selective user access to nursing applications/data and not doctor applications/data may be granted to the nurse. In contrast, according to another approach, in response to receiving the valid user credentials of a user that is a supervising doctor, selective user access to nursing applications/data and doctor nursing applications/data may be granted to the doctor.

According to another embodiment, the type and extent of access to applications/data on the device may be assigned, e.g., by a manager of the medical facility, on an employee to employee basis. Any such assignments may be created, modified and/or revoked at any time.

Decision 108 of method 100 includes determining if a selection of a patient profile corresponding to a patient has been received. The received patient profile selection may correspond with a patient that the user is to perform a wellness check on.

As described elsewhere herein, because patients that are admitted to a medical facility often need to be routinely checked on to maintain their health, wellness checks on patients are performed often throughout the day/night. To conduct a wellness check on a particular patient, a staff member of the medical facility may make a selection of a patient profile.

Method 100 may include outputting a graphical patient profile list to a display of the device. According to one approach, the received patient profile selection may originate as a selection from the patient profile list displayed by the device, e.g., where the selection is performed by a user.

Figure 2:
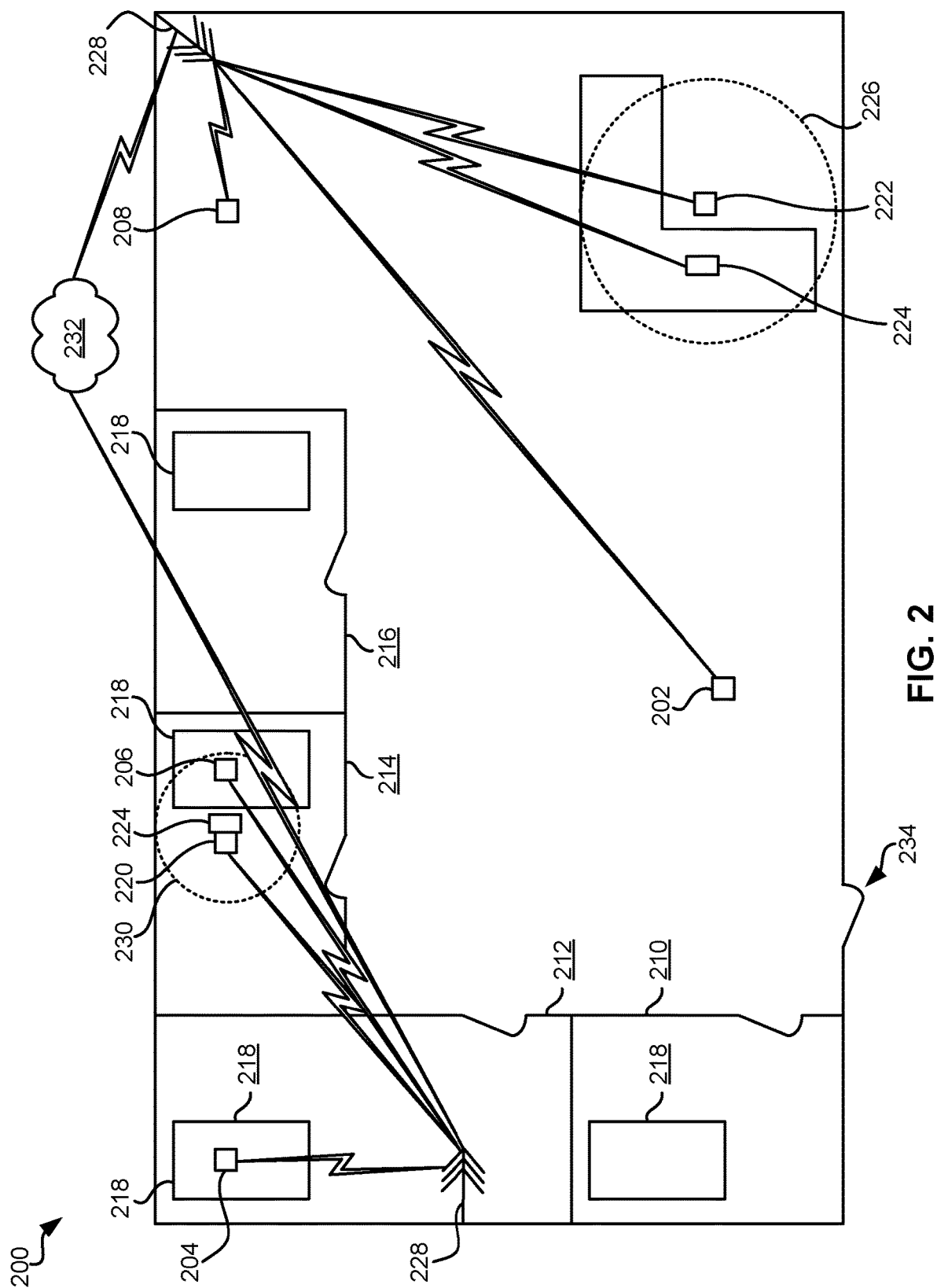
FIG. 2 is an overview of an illustrative medical facility environment, in accordance with one embodiment.

According to another approach, the received patient profile selection may originate as a selection of a patient off of a medical facility map, where the map is displayed by the device for a user that makes the selection, e.g., see FIG. 2. In such an approach, the map may display a most recent known location of the patient. This displayed location may assist the user in finding the patient within the medical facility. According to another approach, the most recent known location of the patient may be received, as will be described in detail elsewhere herein, e.g., see operation 112.

In response to not having received a selection of a patient profile corresponding to a patient, e.g., as illustrated by the "No" logic leading from decision 108, method 100 includes waiting for such a selection to be received.

In response to having received a selection of a patient profile corresponding to a patient, e.g., as illustrated by the "Yes" logic leading from decision 108, the selection of the patient profile may be output, e.g., see operation 110. The received selection of a patient profile may be output in embodiments in which current location data of the selected patient is not stored on the device performing method 100. Location data of the selected patient may assist the user in performing the wellness check, and therefore the output of the selection of a patient profile may be a request for such data. According to various embodiments, the destination of the output may be the medical record library system. According to other embodiments the destination may be any system that includes current location data of the selected patient.

Operation 112 of method 100 includes receiving location data of the patient corresponding to the selected patient profile. According to various embodiments, the location data may include at least a most recent location of the patient of the selected patient profile. Location data of a patient may be collected by a system and/or the device using any known tracking technologies that would be appreciated by one skilled in the art upon reading the present descriptions, as will be described elsewhere herein.

A graphical representation of the location of the patient based on the location data may be output to a display of the device, e.g., see operation 113 of method 100. The graphical representation may be used by the user to find the patient within the medical facility. This assistance in locating patients within the medical facility may be useful for a number of reasons. For example, the graphical representation may allow the user to locate the patient in a much shorter amount of time than would otherwise be possible without the graphical representation. This saved time may correspond to an increase in wellness check efficiency. This saved time may also correspond to fewer untimely wellness checks throughout medical facilities that implement predefined wellness check countdowns. Predefined wellness check countdowns may be recurring time countdown during which a wellness check on a patient is scheduled to be performed. Using the graphical representation of the location of the selected patient may allow the user to quickly locate (and subsequently perform a wellness check on) any patient whose predefined wellness check countdown is close to expiring.

Patients often migrate throughout a medical facility in which they are admitted. For example, one or more patients may migrate to various locations including; group rooms, the kitchen, staff offices, other patient rooms, and open areas of the unit including halls and day rooms. Because the location of any patient may change between the time in which the user views the graphical representation of the last known location of the patient and the time that the user takes to locate the patient, method 100 may include receiving location data of at least one patient every predetermined amount of time. Method 100 may also include updating the display, on the device, with the received location data.

To perform a wellness check, it is important that the user is within a predefined proximity from the patient. As described elsewhere herein, a patient's overall health may be adversely affected in response to a wellness check being performed outside of a proximity of the patient that is required to accurately gather and/or observe wellness data. Decision 114 of method 100 includes determining whether the device is within a predetermined proximity of the patient. According to various embodiments, the predetermined proximity may include any proximate distance that is known to correspond to a user's success in gathering accurate wellness data. According to preferred approaches, the predetermined proximity may be six feet or less. According to another approach, the predetermined proximity may be three feet or less. According to yet another approach, the predetermined proximity may be twelve feet or less. The predefined proximity may vary depending on the patient and/or the type of wellness data being gathered.

In response to a determination that the device is not within the predetermined proximity of the patient, e.g., as illustrated by the "No" logic leading from decision 114, receipt of wellness data of the patient may be denied, e.g., see operation 116. According to one embodiment, an optional operation 118 of method 100 includes the device instructing the user to move within the predetermined proximity of the patient.

In response to a determination that the device is within the predetermined proximity of the patient, e.g., as illustrated by the "Yes" logic leading from decision 114, receipt of wellness data of the patient may be allowed, e.g., see operation 120.

Method 100 may optionally include monitoring the proximity of the user and/or device from the selected patient for a portion of or the entire duration that the user accesses the patient profile. During such monitoring, according to one embodiment, the access to the patient profile may thereafter be revoked in response to the user and/or device not being within a predetermined proximity from the selected patient during the user granted access to the location and wellness data of the selected patient. Revoking access to the patient profile in response to the user and/or device not being within a predetermined proximity from the selected patient may ensure that a user does not simply initially position themselves within the predetermined proximity from the selected patient to gain access to the patient profile, and thereafter falsely attest that they performed the wellness check on the selected patient within the predetermined proximity from the patient when they actually did not do so.

It should be noted that according to one embodiment, the predetermined proximity may additionally and/or alternatively measure the distance between the user and the patient. In such an embodiment, according to one approach, the user may wear a tracking band that is associated with the device, which is used to determine the relative distance between the user and the patient. For example, while administering a wellness check on a patient, a nurse may want to set the device down on a table that is not within the predetermined proximity from the patient. In such an example however, the device may allow receipt of the wellness data in response to a determination that the nurse is within the predetermined proximity from the patient.

According to one embodiment, the wellness data may be data that was recorded and stored by users using the same and/or another device in previous wellness checks of patients. According to another embodiment, the wellness data may have been previously stored to the device during a previous wellness check. A user may use/reference the data (that they were granted access to), while performing a wellness check on the patient. For example, the user may use the received wellness data of the patient as a reference to determine if the overall health of the patient has changed, e.g., improved, stayed about the same, worsened, etc.

According to one embodiment, the wellness data may include at least measured health data and observational data of the patient. According to various approaches, the measured health data (life signs) of the patient may include, e.g., blood pressure, respiratory rates, temperature, etc. According to various approaches, the observational data of the patient may include, e.g., observed body demeanor of the patient, responsiveness, observed tone of voice of the patient, communication conducted with the patient, etc.

It should be noted that some patients may become accustomed to routine wellness checks, and note the duration of time between each administered wellness check so that they know when the next one will be performed. This reality is dangerous and may allow a patient to perform unauthorized and or dangerous activities in the duration of time that the patient knows that he/she will not be receiving a wellness check. For example, such activities may include trying to escape the medical facility, taking a large quantity of medicine that the patient had been hiding instead of taking when administered, trying to commit suicide, etc. To mitigate patients from being able to note the duration of time between each administered wellness check, method 100 may optionally include the device randomly altering the time duration of the predefined wellness check countdown of one or more patients. It should be noted none of the random time durations should exceed a predetermined maximum duration of time between consecutive wellness checks.

Operation 122 of method 100 includes updating the selected patient profile with the location and wellness data, e.g., new location and wellness data that corresponds to data collected during the wellness check of the selected patient. The location and/or process in which the selected patient profile is updated may vary depending on the embodiment.

According to one embodiment, the updating may include outputting, by the device, the location and wellness data to the medical record library. According to one approach, the data may be output by the device to the medical record library using a hardwire connection. According to another approach, the data may be output by the device to the medical record library using a wireless connection.

According to another embodiment, the updating may include storing the location and wellness data, e.g., that corresponds to data collected during the wellness check of the selected patient, to the device. In such an embodiment, the data may be output and/or uploaded by the device to another location, e.g., such as the medical record library system, at some subsequent time.

According to yet another embodiment, the updating may include outputting, by the device, the location and wellness data to one or more other devices, e.g., that are also connected to the medical record library system.

According to another embodiment, the updating may include outputting, by the device, an updated patient profile to one or more other devices, where the updated patient profile reflects the location and wellness data received during the wellness check, e.g., see operation 112. The updated patient profile may be output by the device to any of the destinations previously recited, e.g., a storage component of the device, other devices connected to the medical record library system, the medical record library, etc.

According to one preferred embodiment, the updated patient profile may include a first time stamp, where the first time stamp corresponding to a time the wellness data was received. Including a first time stamp which corresponds to the time the wellness data was received may allow a record to be taken of whether or not a patient has received timely wellness checks. Users such as medical staff members may otherwise forget to record the time in which they perform wellness checks and/or fabricate an inaccurate time in which they attest to having performed a wellness check where they did not, if such time is not automatically recorded by the device. Accordingly, recording the time in which the wellness data was received may ensure honest and accurate workmanship within the medical facility.

According to one embodiment, the first time stamp of the updated patient profile may include an indicator indicative of whether the wellness data was received prior to an expiration of a predefined wellness check countdown of the patient. Any subsequent audit of the patient profile, e.g., by a medical facility administrator, may use the first time stamp indicator to determine whether or not a patient is receiving sufficient care, e.g., timely wellness checks, in the medical facility.

According to another embodiment, the first time stamp may correspond to a time the wellness data was received after an expiration of an unanswered predefined wellness check countdown of the patient. In such an embodiment, the first time stamp may include an indicator that corresponds to a time in which a patient went without a wellness check beyond the expiration of the predefined wellness check countdown of the patient.

Patients of medical facilities can sometimes become irritated/combative and attempt to harm medical facility staff members.

An optional operation of method 100 includes outputting, using the device, a request for emergency assistance in response to a user requiring assistance of any kind. According to preferred approaches, the output request includes location data of the device. The location data of the outputting device may be used by other users that may receive the request for emergency assistance, to locate the user in need of emergency assistance.

It should be noted that outputting the request for emergency assistance from the device instead of emitting the alert through a public address (PA) device may be desirably less disruptive to the medical facility and as a result may set a calmer atmosphere for other patients within the unit.

An optional operation of method 100 includes receiving, using the device, an emergency assistance request from a second device. The received emergency assistance request may include location data of the second device.

According to various embodiments, the emergency assistance request may include an alert. Accordingly, the device may additionally and/or alternatively receive and/or output an alert. The alert may be any type of alert and may vary depending on the embodiment. According to one approach, the alert type may include an emergency assistance request. According to another approach, the alert type may include a patient health alert. According to yet another approach, the alert type may include a notification of at least one approaching expiration of an unanswered predefined wellness check countdown of a patient.

According to one embodiment, method 100 may additionally include outputting a command for a sensory alert to be performed in response to receiving an emergency assistance request from the second device. The sensory alert may be any type of sensory alert, and may vary depending on the embodiment. According to one approach, the sensory alert type may include a vibration. According to another approach, the sensory alert type may include an audio sample. According to another approach, the sensory alert type may include a pulsing visual indicator, e.g., such as a flashing indicator output to the display of the device.

According to various embodiments, in response to an outputting and/or receiving an emergency assistance request, the device may generate a report for the emergency that occurred. The report may include location information of one or more users and/or one or more patients prior to and/or after the emergency assistance request was received and/or output.

According to various embodiments, the location information of one or more users and/or one or more patients may be sampled at predetermined sample rates. The predetermined sample rates may include any amount of time, e.g., fractions of a second, seconds, minutes, etc. For example, in one approach, in response to the predetermined sample rate being set to 1 second, the report generated by the device may include one second sampled location paths of users and/or patients. These sampled location paths may provide someone reviewing the generated report with the path and/or timeliness of users responding to the emergency event. These sampled location paths may additionally provide the location and/or potential involvement that other patients may have had in the emergency event.

According to one embodiment, method 100 may additionally and/or alternatively include receiving an alert when an "at risk" patient enters a high risk location of the medical facility. A "high risk" area may be any location that the at risk patient may pose as a threat to themselves and/or others. At risk patients may include any type of patient that a medical administrator places on a specified and/or heightened monitoring routine. According to various embodiments, an at risk patient may have a medical condition/history that causes the patient to be at risk. According to one approach, an at risk patient may be diabetic. In such an approach, the diabetic at risk patient may be categorized as "at risk" in response to the danger posed that the patient might travel to a kitchen area and consume food that would increase the patient's blood sugar to a dangerous level. According to another example, a high risk area may be a room of a patient that is of the opposite gender of the at risk patient. According to another example, a high risk area may be the exit door(s) of a medical facility and/or floor at which the at risk patient is admitted. It should be noted that high risk areas may be predetermined and/or reassigned by the device at any time. Such assignments may be particular to one or more patients and/or apply to all patients.

It should be noted that patients may be escorted off of the medical facility premises according to one embodiment. In one approach, the device may facilitate such an escorting event in response to receiving a selection of a patient profile, e.g., off of a dropdown menu of patients that are allowed to be escorted off of the medical facility premises. The drop down menu may be incorporated with a wellness check menu. In one approach, the off premises drop down menu may include a notes section for documenting the activities and/or location planned during the off premises escorting. Such activities and/or locations may also be presented by the device in a drop down menu, e.g., listing hospital test appointment, hospital treatment appointment, day treatment appointment, family pass appointment, off hospital grounds with staff, etc.

According to other embodiments, an at risk patient may pose a threat to other patients that share a floor of a medical facility with the at risk patient. According to one approach, a patient may be categorized as at risk in response to the patient having physically combative tendencies. According to another approach, a patient may be categorized as "at risk" in response to the patient being thought to be capable of assault on another patient.

According to various embodiments, the receiving at risk patient alert may include location data of the at risk patient.

FIG. 2 depicts a medical facility environment 200, in accordance with one embodiment. As an option, the present environment 200 may be implemented in conjunction with features from any other embodiment listed herein, such as those described with reference to the other FIGS. Of course, however, such environment 200 and others presented herein may be used in various applications and/or in permutations which may or may not be specifically described in the illustrative embodiments listed herein. Further, the environment 200 presented herein may be used in any desired environment.

It should be noted that environment 200 illustrates an illustrative medical facility for purposes of an example. Any aspect of the facility, e.g., the layout, the patient count, the user count, etc., may vary depending on the embodiment.

Environment 200 includes at least one patient, e.g., see a first patient 202, a second patient 204, a third patient 206, a fourth patient 208. According to various embodiments, the patients 202-208 may each have an assigned room, e.g., see rooms 210-216 (respectively). The rooms 210-216 include beds 218.

Although in the present example, patients 202-208 have assigned rooms 210-216, any of the patients 202-208 may be free to walk about portions of environment 200, e.g., see patients 202, 208 walking about common areas outside of their assigned rooms 210, 216 (respectively).

Each of the patients 202-208 may be assigned and wear a location tracking band. The location tracking band may be used to monitor the location of the patients 202-208 in environment 200, and moreover used to locate the one or more of the patients 202-208, e.g., by a device 224 that is used by a user that is fulfilling a scheduled wellness check on the patient.

Environment 200 also includes at least one user, e.g., see first user 220, second user 222. The job title/responsibilities of the users 220, 222 may vary depending on the embodiment. According to one embodiment, the users 220, 222 of environment 200 may be doctors. According to another embodiment, the users 220, 222 of environment 200 may be nurses. According to another embodiment, the users 220, 222 of environment 200 may be administrative employees, e.g., such as security personnel. According to yet another embodiment, the users 220, 222 of environment 200 may include different combinations of user types, e.g., a doctor and a nurse. Alternatively, according to another embodiment, the users 220, 222 of environment 200 may be of the same user type.

Environment 200 may include one or more devices 224, e.g., for performing method 100. For example the user 220 is illustrated in FIG. 2 holding the device 224 while performing a wellness check on the third patient 206.

Environment 200 includes predetermined proximity areas 226, 230 which as described in method 100, may be assigned to a device 224 and/or a user 220, 222. It should be noted that for purposes of an illustrative example, the user 222 is assigned a predetermined proximity area 226 in environment 200 while the device 224 being used by the user 220 is assigned a predetermined proximity area 230. The dimensions and/or assignments of predetermined proximity areas 226, 230 may vary depending on the embodiment.

Environment 200 may also include antennas 228 of a type that would be appreciated by one skilled in the art upon reading the present descriptions. The antennas 228 are shown in communication with various components of environment 200. For example, the antennas 228 are shown in communication with the location tracking band of each of the patients 202-208. The antennas 228 are also shown in communication with the devices 224 of environment 200.

Communication between the antennas and components of environment 200 may be a part of an established connection between one or more of the devices 224 and a medical record library system 232, e.g., which may include patient profiles.

It should be noted that although the medical record library system 232 is illustrated as a cloud device in environment 200 according to another embodiment, the medical record library system 232 may be a physical library, e.g., such as a server rack, which may be housed on-site in the medical facility.

It should also be noted that although antennas 228 are also shown in communication with the devices 224 and medical record library system 232 of environment 200 according to various other embodiments, one or more of the devices 224 may be in direct communication and/or connected to the medical record library system 232. According to one approach, the direct communication may be established at least in part by an antenna and/or wireless component of the device 224.

Environment 200 may also include one or more predetermined at risk areas, e.g., such as the outside exit 234 of environment 200. The devices may receive an at risk patient alert in response to one or more patients who are not supposed to be in such at risk areas being determined to be entering into and/or be in the at risk area.

Figure 3:
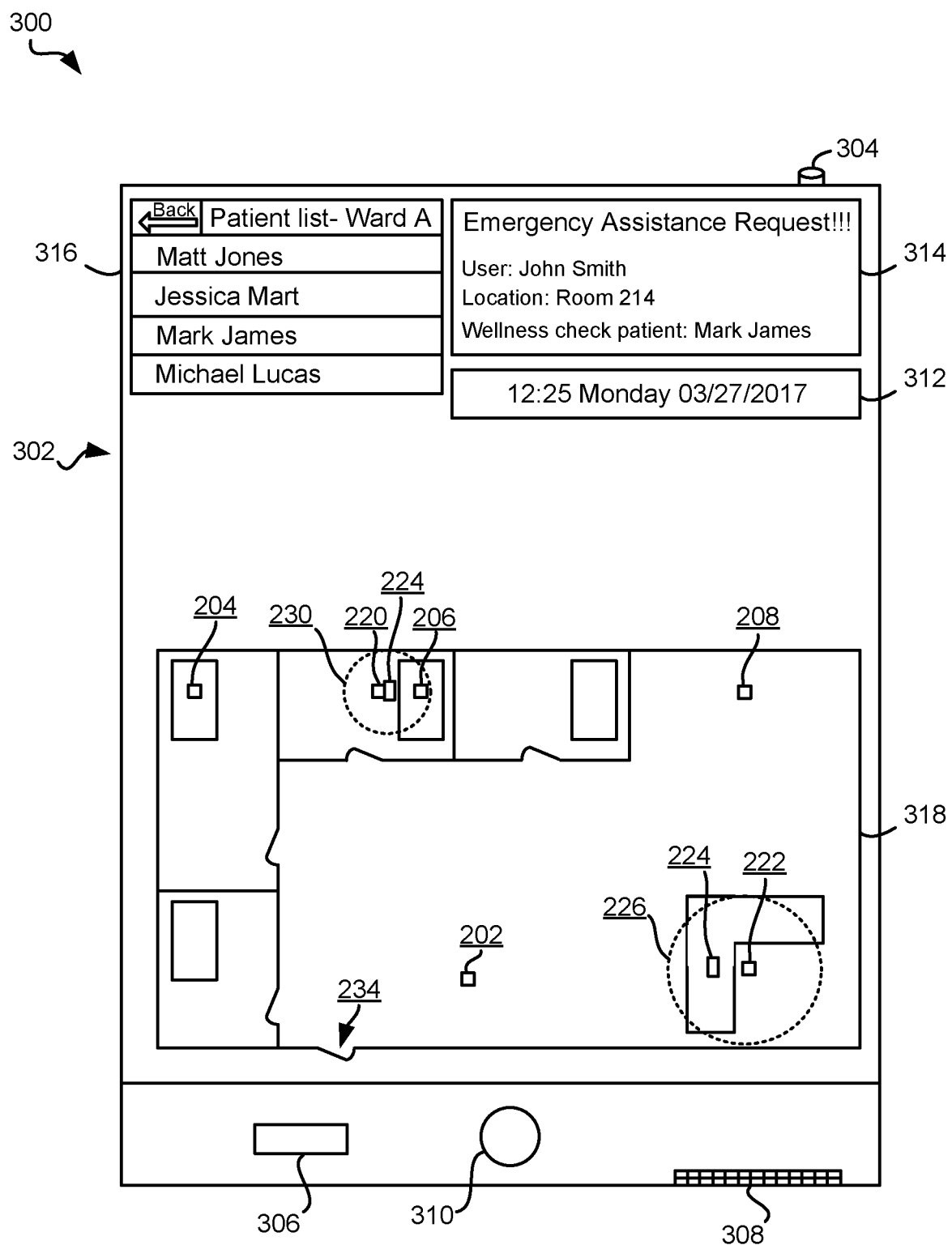
FIG. 3 is a front view of a device, in accordance with one embodiment.

FIG. 3 depicts a device 300, in accordance with one embodiment. As an option, the present device 300 may be implemented in conjunction with features from any other embodiment listed herein, such as those described with reference to the other FIGS. Of course, however, such device 300 and others presented herein may be used in various applications and/or in permutations which may or may not be specifically described in the illustrative embodiments listed herein. Further, the device 300 presented herein may be used in any desired environment.

It should be noted that the device 300 illustrates an illustrative device for performing embodiments described herein, for purposes of an example. Any aspect of the device, e.g., the device layout, applications, illustrative spatial dimensions, etc., may vary depending on the embodiment.

Device 300 includes a display 302. According to one embodiment, the display 302 of the device 300 may include touchscreen capable display. The display may additionally and/or alternatively recognize a selection/writing tool 304, e.g., such as a cursor and use of stylist pen, which may be stored at least partially in the device 300. The selection/writing tool 304 may include "hover" capabilities, where the selection/writing tool 304 is recognized a predetermined distance from the device display 302.

Device 300 also includes an emergency assistance request output button 306. The emergency assistance request output button 306 may be used to request emergency assistance regardless of whether the requesting user is logged into the device or not. This is because the user may not be able to login to the device upon needing emergency assistance, e.g., such as when the user is being physically assaulted by a patient.

One or more speakers 308 may be located on/within the device 300. The speaker(s) 308 may emit user interactive tones and/or in response to receiving an emergency assistance request alert as described elsewhere herein. The device 300 may also include a vibrational component (not shown), which may also emit vibration during use by a user and/or in response to receiving an emergency assistance request alert as described elsewhere herein.

Device 300 may also include one or more other buttons that would be appreciated by one skilled in the art upon reading the present descriptions. For example, device 300 is shown to include a back/home button 310 for device navigation purposes. According to one approach, the button 310 may be used to back out of a user application. According to another approach the button 310 may be used to receive a user access credential, e.g., such as a user fingerprint scan.

Referring again to the display 302 of device 300, the device 300 may output a present time and/or date illustration 312 to the display 302. The present time and/or date illustration 312 may be helpful to a user that is attempting to timely perform wellness checks on patients. The present time and/or date illustration 312 may be synchronized with the master clock so all devices 300 share a common time.

The device 300 may additionally and/or alternatively output an emergency assistance request alert 314 to the display 302. In preferred embodiments, the emergency assistance request alert 314 may be illustrated in an upper right hand corner of the device 300, although the location of the emergency assistance request alert 314 illustration may vary depending on the embodiment. As illustrated in FIG. 3, the emergency assistance request alert 314 illustration may include, e.g., the name of a requesting user (John Smith), location data of the device that output the emergency assistance request (Room 214), the name of a patient which the user was attempting to perform a wellness check on (Mark Janes), etc.

The device 300 may additionally and/or alternatively output a patient name list 316 to the display 302. The patient name list 316 may include the names of patients that correspond to a particular portion of the medical facility and/or the entire medical facility. For example, a user may select a particular medical ward/unit from a dropdown menu of known medical wards/units of a particular medical facility to which the user is assigned to perform wellness checks.

According to one embodiment, a user may tap the location of a user name of the patient name list 316 on the display 302 to access the profile of the selected patient. In response to receiving a selection of a patient from the patient name list 316, the patient profile of the selected patient may be output by the device 300 to all or a portion of the display 302.

According to one embodiment, in response to receiving a selection of a patient from the patient name list 316, the location of a user on a map 318 of the medical facility may be, e.g., highlighted, pulsed, change color, etc.

Referring now to the illustrated medical facility map 318, it should be noted that the medical facility map 318 is similar to the environment 200 illustration of FIG. 2. Accordingly one or more components of the illustrated map 318 of FIG. 3 may share one or more common numberings with the elements of FIG. 2.

The users 220, 222 and/or patients 202-208 of the medical facility map 318 may be visually defined for a user 220, 222 using the device 300.

According to various embodiments, the users 220, 222 and/or patients 202-208 elements on the medical facility map 318 may be defined using color coding and/or number/letter indicators. According to one approach, the type of wellness check and/or duration of a predefined wellness check countdown may be color coded and/or represented by a number/letter indicator. According to one example, a patient that is to be subjected to a wellness check every five minutes in the medical facility may be illustrated on the display 302 as a red colored element on the medical facility map 318 with the number "5" next to the patient's name in the patient name list 316. According to another example, a patient that is to be subjected to constant observation in the medical facility may be illustrated on the display 302 as a black colored element on the medical facility map 318 with the letter "C" next to the patient's name in the patient name list 316. According to another example, a patient that is to be subjected to a wellness check every fifteen minutes in the medical facility may be illustrated on the display 302 as a blue colored element on the medical facility map 318 with the number "15" next to the patient's name in the patient name list 316. According to yet another example, a patient that is to be subjected to a wellness check every thirty minutes in the medical facility may be illustrated on the display 302 as a green colored element on the medical facility map 318 with the number "30" next to the patient's name in the patient name list 316.

According to other embodiments, the users 220, 222 and/or patients 202-208 elements on the medical facility map 318 may be defined using color coding and/or number/letter indicators in response to an emergency. For example, according to one approach, in response to receiving an emergency assistance request, the device may change the displayed color of the user element that represents the requesting user from a standard color, e.g., such as purple, to a known alert color, e.g., such as orange, on the map 318. The user element on the medical facility map 318 may additionally and/or alternatively be pulsed to promote immediate notice.

The device 300 may be of any size and/or shape. The device 300 may preferably have dimensions of 8 inches by 8 inches or 8 inches by eleven inches.

The device 300 may additionally be compatible for using with a protective case. The device 300 display 302 may also include a darkened confidentiality screen for privacy purposes. The display 302 may be selectively and/or sensory toggled from horizontal to vertical viewing, and vise-versa.

The device 300 may also include voice recognition features in one approach.

The following descriptions include illustrative embodiments of the present invention. Any of the following embodiments may be used in conjunction and/or as an alternative to the embodiments described above.

According to one method for performing a patient's wellness check, a tablet device may be connected to a medical electronic record. The tablet device may be used in any type of medical facility. One notable use for the tablet device may be in a psychiatric facility. Many patients of psychiatric facilities require constant observation and a tablet device configured to perform the method(s) and tasks described herein would greatly assist medical staff members who perform such wellness checks.

In addition to assisting medical staff members while performing wellness checks, the tablet device may include other wellness features as well. According to one approach, the tablet device may schedule more oversight of patients and thereby prevent patient fall events. For example in response to a patient having a tendency to fall easily, the device may track the location of the patient and output an alert in response to the patient approaching a fall prone area, e.g., a staircase, a mopped area, bathroom etc.

According to various embodiments, the tablet device may be compatible with other conventional medical facility equipment and/or software. The tablet device may additionally and/or alternatively be connected to any main computer system that the medical facility is already using. According to one approach, in response to being connected to any existing medical facility system(s) the tablet device will be able to upload data to the medical facility system. According to another approach, the tablet device may be compatible with any magnetic battery chargers in the medical facility and/or any functionalities of portable medical staff member's work stations, e.g., such as a nurse's station which may include upload and/or charging ports. Such meshing between the tablet device and existing medical facility operations/components may enable the tablet device to function with the existing hospital medical electronic record.

According to one embodiment establishing a connection between the tablet device and existing medical facility operations/components may enable the device to be used for other functionalities, e.g., recording patient admissions, recording patient discharges, recording patient room changes, etc.

The tablet device may be compatible with and/or use any technology to receive and/or send data, e.g., data that is associated with a wellness check, previously recorded patient data, location data, etc. According to one approach, the tablet device may be compatible with and/or use GPS technology. GPS technology may be used for tracking/recording location information of a patient and/or user of the tablet device, e.g., such as a staff member, as described elsewhere herein.

The GPS technology may include one or more patients and/or one or more users wearing a tracking locator. According to one approach, the tracking locator may include a GPS enabled watch. According to one approach, the tracking locator may include a name band with a tracking chip in the name band. In such an approach the tracking chip may include any type of tracking chip, e.g., a radio frequency identification device (RFID) chip, a GPS chip, a triangulation location chip, a proximity based detection chip, etc.

Referring again to the display of the device, the device may output an outlay of all and/or a portion of the medical facility, e.g., herein referred to as a map of the medical facility. The map may include patient elements, e.g., dots where each of the illustrated dots is a patient and/or user.

As described elsewhere herein, according to various embodiments, the patient elements may be color coordinated for any type of patient and/or user type. According to one approach, the female patient elements may be pink and male patient elements may be blue. This contrast in colors may be useful in medical facilities where male patients are not allowed in female patient rooms, and vise-versa. According to another approach, a black colored patient element may represent that the patient is "gender neutral." A patient's assigned gender and/or patient element color may be selected, e.g., by an administrator, from a drop down menu that is output to a display of the device by the device.

According to various embodiments, the device may be configured to use lost device locating applications. With such applications, if someone misplaces their device, they can find it.

As described elsewhere herein, the device may record the location of patients relative to users and/or vise-versa. This feature may be useful as it may clarify any allegations that may be made against staff members of the medical facility.

The device may also be configured to assign one or more patients to a group. Medical facilities often seat similar patient types in group programs, e.g., for discussion, therapy, exercise, etc., where the group may be managed by a group leader or medical professional. A group assignment on the device may assist the group leader or medical professional that is working with the group. For example, the group leaders may tabulate who they have in that group and/or if a patient of that group physically leaves the group.

Any group leader or medical professional that is working with the group may have be required to be within a predetermined proximity when performing a patient wellness check on any one or more patients of the group. The predetermined proximity may be assigned by one or more users of the device and/or system managers of the system in which the device is connected. The predetermined proximity may ensure that the user is within an appropriate distance from the patient when performing a wellness check, e.g., and not somewhere else in the medical facility where they would not be able to adequately perform the wellness check.

As described elsewhere herein, the display of the device may also illustrate a patient list of patients of the medical facility. According to one approach, a user may touch a displayed patient element and on the lower half of the screen the patient name may be illustrated in response to the selection. In response to a user touching the subsequent illustration the name and the room number may be illustrated. The selection may also navigate the user to a wellness check grid, where the wellness check grid may receive data that corresponds to a wellness check of the selected patient.

Real-Time Tracking System Features

The device may also include a real time user/patient location tracking feature.

According to one approach, the real time user/patient location tracking feature may track the location of patients and/or users using any one or more of: satellite tracking, GPS Satellite Tracking, GPS tracking systems, etc.

The real time user/patient location tracking feature may instantly identify the patient and the patient's location, with the time and date, in real-time. The feature may be connected/associated with the mapping feature described elsewhere herein, and/or any other real-time locating system (RTLS).

According to one approach, the real time user/patient location tracking feature may be enabled by wireless systems, suitable for contained areas. Such an embodiment, may include system-level deployments and server functions to be effective.

According to another approach, the real time user/patient location tracking feature may include a bar-code scanning functionality/system. Such an approach may include: barcode scanning and/or RFID scanning. Automatic identification of patient may be available via wristband barcode scanning, e.g. scanning a quick response (QR) code. Accordingly, the device may include one or more cameras and/or barcode scanners.

It should be noted that an infrared stamp may be applied to the skin and or clothing of a patient, where the stamp may be scanned by the device. The device may scan a patient's stamp, e.g., for patient identification, per an administering of medication, per entrance/output of a group, etc.

According to another approach, the device may be used for managing the administering medications to a patient. In such an approach, the real time user/patient location tracking feature may be used to locate the patients for medication administering. Such an approach may include locating one or more patients using any one of the location tracking types described elsewhere herein.

It should be noted that if a real time tracking feature loses connection with real time tracking devices, e.g., such as a satellite or antenna, the device may output an alert or tone to notify the user of a loss of connectivity.

According to another approach, the device may include a compartment with the medicine of one or more patients. The medication may be selectively dispensable upon determining that the device is within a predetermined proximity from patient that is to receive the medication.

According to another approach, the real time user/patient location tracking feature may be used with patient wristbands. A patient's wristband may be embedded with a chip, e.g., that identifies the patient, that identifies the location of the patient, that identifies the patient's doctor's name, that identifies the patient's room number, that identifies the patient's identification barcode, that identifies if the patient is considered an at-risk patient, etc.

A patient that is designated at risk may be illustrated on the device map as a patient element with the color yellow. At risk areas for at risk patients may be designated on the tablet. For example, exit doors may be designated as at risk areas, so if a patient goes near an exit door, the color of the patient may be pulsed or change from a standard patient element color to yellow, or another designated color on the device map.

According to another example, the medical facility may implement electronic geography (GEO) fences that fence off high risk areas of the facility or unit. A diabetic patient, for example, may not be allowed to go to certain areas of the unit, such as to the kitchen where eating food could dangerously increase the at risk patient's blood sugar level. The device may receive an alert from the geo fence that the at risk patient is entering an at risk area. In response to the at risk patient going near the kitchen, the device may display the at risk patient's element on the map with the color yellow, and/or a tone alert and a user that sees the yellow patient and/or hears the tone alert element may respond and prevent a problem from occurring.

The device may also display the at risk patient's element on the map with the color yellow, or some other color, in response to a patient of one gender entering the room of another patient of the opposite gender.

According to one embodiment, a patient's name displayed on the device may match/correlate to the patient's wristband. According to one approach, a patient wristband may incorporate a FITBIT® bracelet/watch component to use in tracking patient's pulse. If the device receives data that shows that a patient's pulse has fallen below a predetermined pulse rate, the device may output an alarm and/or notification. products may be purchased at FITBIT® headquarters which is located at 405 Howard Street suite 550, San Francisco, Calif. 94105, or other various sale locations.

Data, e.g., pulse rates, received by the device from patients wearing a FITBIT® bracelet/watch component may be output by the device to the device display. For example, such data may be output to the lower right hand corner of the device display.

According to one approach, the real time user/patient location tracking feature may perform updating of a patient profile using a magnetic battery charger. The updating may be output to a main nurse station via a port connection according to one example.

According to another approach, the real time user/patient location tracking feature may include wireless data capture-collecting of information. Such information may be saved to the medical library system database. The device may also receive updated current patient list(s), including at least the patient's name and room number, e.g., where the updates occur in response to other users performing wellness checks. The received updates may also include one or more of patent admissions, patent discharges, patent room changes, etc.

According to another approach, the real time user/patient location tracking feature may include bar code recognition (BCR) technology. BCR technology enable information to be extracted from paper documents, e.g., such as wrist bands, for further processing.

It should be noted that the real time user/patient location tracking feature may be initiated in response to a receiving event. According to one approach the receiving event may include receiving a valid user access credential. According to one approach the receiving event may include a patient profile selection, e.g., from a user.

Referring again to general various embodiments of the device, it should be noted that while and/or after performing a wellness check on a patient, a user may record a note/comment on the patient profile of the selected patient.

According to one approach, the note may be received and stored to the device and/or output by the device to the medical record library system, e.g., for real time updating of the selected patient profile. Such notes may provide a user with an idea of how the selected patient is doing that day. This may be very valuable information as a user will be updated with information that other users have recorded prior to the user contacting the selected patient.

It should be noted that all data and patient profiles may comply with the Health Insurance Portability and Accountability Act of 1996 (HIPAA).

The device may according to various embodiments include a printer and/or be configured to output one or more selected documents to be printed.

Data of the real-time tracking system feature may be stored and/or output for future access and/or display, e.g., such as upon request by a user of the device. According to one preferred embodiment, the device may store the history of wellness checks, e.g., times that the checks were performed, locations of a patient, locations of a patient when the patient is not receiving a wellness check, etc., where the stored data may be later displayed by the device in response to receiving a patient profile selection. For example, past location information of a patient may be displayed on the display of a device in response to receiving a patient selection off of a drop down menu displayed by the device. This may be useful to be able to see where the patient has been earlier in the day or for a shift for staff to gather information and evaluate patient progress.

Patient Grouping Features

As described in other embodiments elsewhere herein, the device may receive assignments of patients to particular patient groups. Group leaders may use the device to register patients in a particular group. Any received assignments may be output by the device to other devices.

One or more devices used by group leaders may selectively output information to other users, e.g., notification that a patient is agitated or acting inappropriately while in the group. Any patients assigned to a group may be illustrated on the map of a device display.

According to other embodiments, patients with similar predefined wellness check countdowns may be assigned to a group. Such groupings may be assigned by the device for an experienced user to perform wellness checks on so that the countdown does not expire prior to a wellness check being performed.

Patient Intake Process of an Illustrative Psychiatric Unit

According to various embodiments, a patient intake process may be initiated in response to a patient arriving at a psychiatric unit medical facility. Although the present example is described to occur at a psychiatric unit of a medical facility, the type of medical facility may vary depending on the embodiment.

A user such as a charge nurse or secretary may registers the patient in the medical facility database. The database may be used by the entire medical facility, or alternatively just the psychiatric unit.

The patient may be given a printed wristband that has a chip embedded in it that identifies, e.g., the patient's name, the patient's location, the patient's doctor's name, the patient's room number, an identification barcode, if the patient is a high risk patient, etc. The chip can be embedded into clothing or on the skin with an adhesive (similar to nicotine patch adhesive), if the patient refuses to wear the wristband.

The patient's information on the wristband may be matched and automatically downloaded by one or more devices used in the medical facility or psychiatric unit. Additionally, the pulse rate of a patient using a FITBIT® wristband may be tracked and/or downloaded by the device. FITBIT® wristbands or similar monitoring devices may be useful to determine if a patient is sleeping or beginning to enter into a coma, e.g., as a result of a medication overdose.

The device may be logged into by a user using a unique personal code, e.g., such as the user's fingerprint, a user selected code, a badge ("tap-in/tap-out" method).

The user may view a map of the psychiatric unit output by the device to a display of the device. The display may display an initial mobile dot screen, e.g., where mobile patient dots depict patients and/or users of the psychiatric unit.

According to one approach, the lower half of display may display a patient highlight screen, e.g., including a list of patients admitted to the psychiatric unit. In the patient highlight screen, the user may select a patient profile. In response to receiving a patient profile selection, the device may highlight the patient name and/or note the location of the selected patient on the mobile dot screen, e.g., on the upper half of the screen.

The patient highlight screen can be accessed by a user without the device receiving a selection of the patient element on the displayed map. According to one approach, an entire list of patients of a particular medical facility or a selective portion of the medical facility may be displayed by the device on the patient highlight screen.

Once the user selects a patient, the user may select an option of either: "Open Chart" (this is the entire patient chart stored in the medical electronic record or "Open Wellness Check". In response to receiving an "Open Wellness Check" selection, a "Wellness Check Grid Screen" may be opened and/or generated.

Users may use up to three or even more screen icons while performing a wellness check, e.g., a Mobile Dot Screen map, the patient highlight screen, the wellness check grid screen. It should be noted that the size and/or positioning of any one or more icons may be altered and/or zoomed in/out, in response to receiving an input, e.g., from a user's touch selection.

In response to receiving an "Open Chart" menu selection an order for a particular type of wellness check may be assigned by the device for the new patient. The assignment may be made by a user such as a doctor making the selection on the device. A user may select an "Orders" tab (in the medical electronic record) to view the type of wellness check that was assigned. The device may also and/or alternatively present the option to initiate or change the wellness check time intervals, e.g., in accordance with Doctor's orders to 5, 15, 30 minute checks or constant observation status, in the Medical Electronic Record. Any changed wellness check time intervals may be output by the device to one or more other devices.

The device may receive an "Open Wellness Check" selection from a drop down menu on the Patient Highlight Screen. The selection may correspond to a subsequently identified patient profile, e.g., selection received from a user tapping the initial mobile dot screen. In response to receiving the selection, device may highlight the patient's information in the lower half of the screen.

The device may also identify/highlight the selected patient on the patient highlight screen and/or the mobile patient dot on upper half of screen. Either selection may show the patient's location.

Data, corresponding to a performed wellness check on the selected patient, may be added to the patient's data grid.

The user may wish to confirm that the type of wellness check listed on the device complies with the Doctor's orders.

As previously described on any icon the patient's name may be color coded, e.g., in accordance with the at risk nature of the patient, the predefined wellness check countdown of the patient, etc.

It should be noted that the device may generate a report for any icon of the device at any time, including the Mobile Dot Screen in real time.

Patient Discharge

The device may record the time that a patient is discharged from the medical facility. The device may record the time that a patient is discharged from the medical facility in response to receiving a "discharge patient" selection from a displayed tab, in the drop-down menu of the wellness check grid screen.

Performing a Patient Wellness Check

According to one embodiment, a patient wellness check process may be initiated in response to a user logging into a device.

While a user is logged into a device, the location of the staff and/or device may be recorded. The location of the device may also be displayed on other devices, e.g., such as by a green square staff/location element, the same size as a patient element.

The device may display the location of a patient in response to receiving a user patient selection.

According to various embodiments the device may display a queue that sequentially orders patients according to the remaining time left in each patient's wellness check countdown. This ordering may provide a user that is performing wellness checks with a priority of which patient needs to be checked on next.

According to one embodiment, in response to a patient's wellness check countdown reaching a predetermined amount of time prior to expiration, e.g., two minutes, the device may output (to the device display) a countdown timer listing the time left in the approaching countdown expiration. The output countdown timer may be included in a noticeably colored icon and list the patient location information. The countdown icon may be terminated in response to the wellness check for the patient with the approaching countdown expiration being fulfilled. If a patient's wellness check countdown expires prior to being fulfilled, the patient's name may change color on the patient wellness check grid, in order to notify staff that the wellness check is late. According to one approach, the countdown timer color may change approaching a time window, e.g., a 2 minute window, prior to the check, to alert staff that the check needs to be done immediately and to prioritize checks.

The device may redirect a user to the patient wellness check grid in response to the user selecting a patient's name and/or map element.

The user may perform the scheduled wellness check on the selected patient. As described elsewhere herein, the device may selectively grant the user access to the selected patient profile in response to determining that the user is within a predefined proximity from the patient.

In response to receiving a patient profile selection, the device may grant the user access to the patient profile. The device may receive wellness check information from a wellness check performed on the selected patient.

The device may end the wellness check in response to receiving a selection of the user's initials and/or name which may be displayed on the display.

For reference, according to one embodiment, a bird's eye view of the patient wellness check grid may include the patient's name, room number, doctor, high risk assignment, etc. on the left portion of the display. The top of the grid may display the designated increment of time remaining before expiration of a wellness check countdown, e.g., 5 minutes, 15 minutes, 30 minutes, etc. The bottom of the grid may display staff initials for ending the wellness check recording. In one approach the user's full name may be displayed for selecting by the device in response to receiving a selection of the initials. The middle of the displayed grid may include a red box that shows the current time, the location of a patient, the pulse rate of a patient. The right side of the display may include one or more drop down menus.

For reference, according to one embodiment, a bird's eye view of the red box in the grid may include a current time and current location in the center of the red box. An asterisk to indicate a comment or life signs that correspond to the patient in the upper left hand corner of the red box. A pulse rate of the patient, e.g., if patient is wearing a FITBIT®, in the lower right hand corner of red box.

For reference, according to one embodiment, a drop down menu at the top right corner of the grid may include one or more information types. One information type may include life signs of a patient. According to one example, the life signs may include: awake and resting, observed rise and fall of chest in breathing, patient movements, eyes closed, sitting in room or on bed, snoring, laying on bed or in bed, verbally responds to user, difficult to arouse. A vital sign (pulse) may populate on the Grid and in the "All Results" section of the "Open Chart" (Medical Electronic Record).

Another information type may include activities: where the activity choices may include: in bed (ib), on bed (ob), with staff (S), in kitchen (K), in group (grp), on unit (ux), bathroom (br).

Another information type may include room assignment change(s).

Yet another information type may include orders.

Another information type may include discharges of one or more patients, see described elsewhere herein.

Another information type may include comments. In response to a comment being selected, an asterisk may be displayed by the device in the red box of the grid. Comments may also auto populate in the chart under a "Comments and Life Signs during Rounds" icon. Nurses or other users may review these comments before they write their "Nurses Note".

Another information type may include geo-fencing which may include an add and/or remove geo-fencing option.

The displayed time in the red box of the wellness check screen grid may be stopped to indicate the exact time of the wellness check, and the box may be transitioned to another color, e.g., black. The device may display the countdown timer of the next check in the next grid box (for the next wellness check to be performed).

The device may accumulate the time, date and/or location of patients and/or users into a report. At the end of a user's shift, or any time before then, this report can be printed out.

These reports may be verified to ensure that the wellness checks were accurate and performed according to set standards. The verifier may print the reports, sign the reports, and/or submit the reports online, e.g., using the device.

Device Use by Group Leaders and/or Doctors

As described elsewhere herein, devices may operate in accordance with assigned patient groups. A group leader may select the specific group name or type of group from a drop-down menu of the device in the "Group Section", of the drop-down menu, in the "Open Chart" section of the medical electronic record. The "Group Section" also may be in the drop-down menu on the wellness check grid screen.

The device may populate the assigned group in accordance with the received group members. The group may also be displayed on a map of the device display. The device may also populate the wellness check grid screen to show the patients that are "in group" (ig).

According to one embodiment, the device may output a distinguishable tone (such as a doorbell sound) to alert one or more users of the medical facility when a patient of the group leaves the group in mid-session. The tone may alert a user (such as a nurse that is performing rounds) to "uncheck" the patient from group, when in response to the patient leaving the group.

The device may receive notes recorded by the group leaders on the device detailing the group's progress.

The device may receive an end group command indicating the group has ended its session. A selection to end the group session may be displayed by the device in a drop-down menu in the "Group Section" of the display.

The device may output a notification to a user that is performing rounds that the group has ended. A device used by the user performing rounds may receive the output notification of the ending session. According to one approach the notification may populate an icon on the Wellness Check Grid Screen of the device of the user performing rounds.

A distinguishable tone may be output by the group leader's device in response to the session being ended.

If a Doctor or other staff member wishes to meet up with a patient or group, the Doctor or other staff member may locate the group using the map of the display or the drop-down menu of locations on the device display which may indicate where the group is meeting. The drop-down menu may be located in the "Open Chart" of the medical electronic record and/or in the drop-down menu of the wellness check grid screen, in the "Meeting with Patient" section of the device interface. The location of group meetings may be set by any one or more users and updated on the device in response to the device receiving the group meeting location.

Real-Time Patient Charting

As described in detail elsewhere herein, the device may include the medical record for each patient in a medical facility. These records may be updated by the device in response to receiving progress notes and patient wellness data that corresponds to a wellness check performed on a patient.

The device may receive user data, patient notes and update the profile of patients in "real-time."

A user may select the "Open Chart" tab or the "Open Wellness Checks" tap to record a patient note or wellness data of a selected patient. In response to the "Open Wellness Checks" tab being selected, the device may display a wellness check grid icon, which may include a drop-down tab for "Nurses Note".

According to one approach, in response to the "Open Chart" tab being selected, the "Nurses Note" tab may be presented by the device in the medical electronic record.

A device may receive a note from a user performing wellness rounds. The device may store and/or output to other devices the comment. One or more devices may present the comment in the "Comment Section" of the display, e.g., to provide additional information to staff of the medical facility, in real-time. The "Comment Section" or the "nurses note" may be located in the wellness grid portion in the device drop down menu.

Various embodiments described herein may be performed using a computer program product. The computer program product may include a computer readable storage medium having program code stored thereon. The program code may be executable by a device to cause the device to perform a process described in such embodiments. The computer readable storage medium may be a non-transitory computer readable storage medium.

The inventive concepts disclosed herein have been presented by way of example to illustrate the myriad features thereof in a plurality of illustrative scenarios, embodiments, and/or implementations. It should be appreciated that the concepts generally disclosed are to be considered as modular, and may be implemented in any combination, permutation, or synthesis thereof. In addition, any modification, alteration, or equivalent of the presently disclosed features, functions, and concepts that would be appreciated by a person having ordinary skill in the art upon reading the instant descriptions should also be considered within the scope of this disclosure.

While various embodiments have been described above, it should be understood that they have been presented by way of example only, and not limitation. Thus, the breadth and scope of an embodiment of the present invention should not be limited by any of the above-described exemplary embodiments, but should be defined only in accordance with the following claims and their equivalents.

What is claimed is:

1. A device-implemented method for improving health of one or more patients as a result of performing a patient wellness check in a manner that prevents a staff member from entering false data in a patient's profile, comprising:
   connecting a device to a medical record library system;
   outputting, by the device, a login interface to a touchscreen display of the device for displaying thereon;
   in response to detecting receipt of a valid user access credential on the touchscreen display of the device, granting, by the device, selective user access to the device, wherein granting the selective user access includes outputting, to the touchscreen display of the device, applications pre-associated with a job title of a user associated with the valid user access credentials;
   in response to detecting receipt of a predetermined number of invalid user access credentials on the touchscreen display of the device within a predetermined amount of time, outputting, by the device, a timed out login interface to the touchscreen display of the device for displaying thereon;
   outputting, by the device, a map illustration to the touchscreen display of the device, wherein the map illustration includes graphical icons each representative of locations of an associated patient, wherein a color of a portion of each of the graphical icons is based on a current remaining predefined wellness check countdown of an associated one of the patients;

detecting, by the device, receipt of a selection on the touchscreen display of the device, the selection being detected on a portion of the touchscreen display corresponding to a patient profile of a patient;

receiving, by the device, location data of the patient corresponding to the selected patient profile, wherein the location data includes at least a most recent location of the patient of the selected patient profile;

outputting, by the device to the touchscreen display of the device, an updated map illustration, the updated map illustration including a graphical icon representative of the most recent location of the patient based on the location data;

determining whether the device is within a predetermined proximity of the patient;

allowing, by the device, receipt of wellness data of the patient in response to a determination that the device is within the predetermined proximity of the patient, thereby ensuring that a staff member using the device is not able to falsely attest to being within the predetermined proximity of the patient during attempted submission of the wellness data where the staff member is in actuality outside of the predetermined proximity of the patient during the attempted submission of the wellness data, wherein allowing receipt of wellness data of the patient includes allowing receipt of data input by touchscreen, wherein the wellness data includes at least measured health data and observational data of the patient, wherein the observational data was previously input by at least some staff member(s) using the device;

denying receipt of the wellness data in response to a determination that the device is not within the predetermined proximity of the patient, thereby ensuring that the staff member using the device is not able to falsely attest to being within the predetermined proximity of the patient during attempted submission of the wellness data where the staff member is in actuality outside of the predetermined proximity of the patient during the attempted submission of the wellness data, wherein denying receipt of wellness data of the patient includes disabling receipt of data input by touchscreen;

allowing, by the device, receipt of wellness data of the patient in response to a determination that the device is not within the predetermined proximity of the patient but the staff member is within the predetermined proximity of the patient, thereby ensuring that the staff member using the device is not able to falsely attest to being within the predetermined proximity of the patient during attempted submission of the wellness data where the staff member is in actuality outside of the predetermined proximity of the patient during the attempted submission of the wellness data, wherein allowing receipt of wellness data of the patient includes allowing receipt of data input by touchscreen;

updating, using the device, the selected patient profile with the location and wellness data, wherein the updated patient profile includes a first time stamp, the first time stamp corresponding to a time the wellness data was received and includes an indicator indicative of whether the wellness data was received prior to an expiration of a predefined wellness check countdown of the patient; and modifying, by the device, a time duration of the predefined wellness check countdown of the patient a random amount.

2. A device-implemented method as recited in claim 1, wherein the updating the selected patient profile includes outputting, by the device, the location and wellness data to the medical record library system.

3. A device-implemented method as recited in claim 1, wherein the access to the patient profile is thereafter revoked in response to a determination that the device is not within a predetermined proximity from the patient associated with the selected patient profile during the granted access to the location and wellness data of the patient associated with the selected patient profile, thereby ensuring that a staff member using the device is not able to falsely attest to being within the predetermined proximity of the patient during obtaining of the wellness data where the staff member is in actuality outside of the predetermined proximity of the patient during the obtaining of the wellness data, wherein the determining whether the device is within a predetermined proximity of the patient is initially determined based on a scanning performed on an infrared stamp previously applied to skin of the patient of the selected patient profile.

4. A device-implemented method as recited in claim 1, comprising: outputting, by the device, a request for emergency assistance, wherein the output request includes location data of the device.

5. A device-implemented method as recited in claim 1, comprising:

receiving, using the device, an emergency assistance request from a second device, wherein the received emergency assistance request includes location data of the second device, wherein the device is not in a line of sight of the second device at a time at which the emergency assistance request is received from the second device; and recording relative locations of the staff member with respect to the patient of the selected patient profile to serve as a reference thereafter in an event that the patient of the selected patient profile makes an allegation against the staff member.

6. A device-implemented method as recited in claim 1, comprising: receiving, by the device, an alert, wherein a type of the alert is a notification of at least one approaching expiration of an unanswered predefined wellness check countdown of a patient.

7. A device-implemented method as recited in claim 1, wherein the access credential is an audio sampling.

8. A device-implemented method as recited in claim 1, comprising: receiving, on the device, location data of at least one patient every predetermined amount of time; and updating a display, on the device, with the received location data.

9. A device-implemented method as recited in claim 1, wherein a first extent of selective user access to the device is granted in response to a determination that the received valid user access credential is that of a nurse, and wherein a second extent of selective user access to the device is granted in response to a determination that the received valid user access credential is that of a supervising doctor.

10. A device-implemented method as recited in claim 1, comprising:

instructing dispensing, from the device, medication for the patient in response to a determination that the device is within the predetermined proximity of the patient;

in response to detecting, by the device, the receipt of the predetermined number of invalid user access credentials on the touchscreen display of the device within a predetermined amount of time, outputting, by the device, a notice message to a manager of a system that includes the device, wherein the notice message indicates the detected receipt of the predetermined number of invalid user access credentials on the touchscreen display of the device within a predetermined amount of time, wherein the portion of the touchscreen display corresponding to the selected patient profile displays a drop down menu prior to the selection being detected, wherein the portion of the touchscreen display displays a notes section within a drop down menu;

receiving, using the device, an emergency assistance request from a second device, wherein the received emergency assistance request includes location data of the second device, wherein the device is not in a line of sight of the second device at a time at which the emergency assistance request is received from the second device;

recording relative locations of the staff member with respect to the patient of the selected patient profile to serve as a reference thereafter in an event that the patient of the selected patient profile makes an allegation against the staff member; and in response to a determination that an emergency assistance output button of the device has been pressed, outputting, by the device, location data of the device to at least the second device, wherein the access to the patient profile is thereafter revoked in response to a determination that the device is not within a predetermined proximity from the patient associated with the selected patient profile during the granted access to the location and wellness data of the patient associated with the selected patient profile, thereby ensuring that a staff member using the device is not able to falsely attest to being within the predetermined proximity of the patient during obtaining of the wellness data where the staff member is in actuality outside of the predetermined proximity of the patient during the obtaining of the wellness data, wherein the determining whether the device is within a predetermined proximity of the patient is initially determined based on a scanning performed on an infrared stamp previously applied to skin of the patient of the selected patient profile.

11. A computer program product for improving health of one or more patients as a result of performing a patient wellness check in a manner that prevents a staff member from entering false data in a patient's profile, comprising a non-transitory computer readable storage medium having program code stored thereon, the program code executable by a device to cause the device to perform a process comprising:

connecting, by the device, to a medical record library system;

outputting, by the device, a login interface to a touchscreen display of the device for displaying thereon;

in response to detecting receipt of a valid user access credential on the touchscreen display of the device, granting, by the device, selective user access to the device, wherein granting the selective user access includes outputting, to the touchscreen display of the device, applications pre-associated with a job title of a user associated with the valid user access credentials;

in response to detecting receipt of a predetermined number of invalid user access credentials on the touchscreen display of the device within a predetermined amount of time, outputting, by the device, a timed out login interface to the touchscreen display of the device for displaying thereon;

outputting, by the device, a map illustration to the touchscreen display of the device, wherein the map illustration includes graphical icons each representative of locations of an associated patient, wherein a color of a portion of each of the graphical icons is based on a current remaining predefined wellness check countdown of an associated one of the patients;

detecting, by the device, receipt of a selection on the touchscreen display of the device, the selection being detected on a portion of the touchscreen display corresponding to a patient profile of a patient;

receiving, by the device, location data of the patient corresponding to the selected patient profile, wherein the location data includes at least a most recent location of the patient of the selected patient profile;

outputting, by the device to the touchscreen display of the device, an updated map illustration, the updated map illustration including a graphical icon representative of the most recent location of the patient in response based on the location data;

determining, by the device, whether the device is within a predetermined proximity of the patient;

allowing, by the device, receipt of wellness data of the patient in response to a determination that the device is within the predetermined proximity of the patient, thereby ensuring that a staff member using the device is not able to falsely attest to being within the predetermined proximity of the patient during attempted submission of the wellness data where the staff member is in actuality outside of the predetermined proximity of the patient during the attempted submission of the wellness data, wherein allowing receipt of wellness data of the patient includes allowing receipt of data input by touchscreen, wherein the wellness data includes at least measured health data and observational data of the patient, wherein the observational data was previously input by at least some staff member(s) using the device;

denying, by the device, receipt of the wellness data in response to a determination that the device is not within the predetermined proximity of the patient, thereby ensuring that the staff member using the device is not able to falsely attest to being within the predetermined proximity of the patient during attempted submission of the wellness data where the staff member is in actuality outside of the predetermined proximity of the patient during the attempted submission of the wellness data, wherein denying receipt of wellness data of the patient includes disabling receipt of data input by touchscreen;

allowing, by the device, receipt of wellness data of the patient in response to a determination that the device is not within the predetermined proximity of the patient but the staff member is within the predetermined proximity of the patient, thereby ensuring that the staff member using the device is not able to falsely attest to being within the predetermined proximity of the patient during attempted submission of the wellness data where the staff member is in actuality outside of the predetermined proximity of the patient during the attempted submission of the wellness data, wherein allowing receipt of wellness data of the patient includes allowing receipt of data input by touchscreen;

updating, using the device, the selected patient profile with the location and wellness data, wherein the updated patient profile includes a first time stamp, the first time stamp corresponding to a time the wellness data was received and includes an indicator indicative of whether the wellness data was received prior to an expiration of a predefined wellness check countdown of the patient; and modifying, by the device, a time duration of the predefined wellness check countdown of the patient a random amount.

12. A computer program product as recited in claim 11, wherein the updating the selected patient profile includes outputting, by the device, the location and wellness data to the medical record library system.

13. A computer program product as recited in claim 11, wherein the selective user access to the device includes access to the selected patient profile, wherein the access to the patient profile is thereafter revoked in response to a determination that the device is not within a predetermined proximity from the patient associated with the selected patient profile during the granted access to the selected patient profile, thereby ensuring that a staff member using the device is not able to falsely attest to being within the predetermined proximity of the patient during obtaining of the wellness data where the staff member is in actuality outside of the predetermined proximity of the patient during the obtaining of the wellness data, wherein the determining whether the device is within a predetermined proximity of the patient is initially determined based on a scan performed on a wristband quick response (QR) code.

14. A computer program product as recited in claim 13, comprising program code executable by the device to cause the device to reinstate the access to the patient profile in response to receiving a modification of an extent of the selective user access, wherein the modification is received from a manager of a medical facility.

15. A computer program product as recited in claim 11, comprising program code executable by the device to cause the device to output a request for emergency assistance, wherein the output request includes location data of the device.

16. A computer program product as recited in claim 11, comprising program code executable by the device to cause the device to receive an emergency assistance request from a second device, wherein the received emergency assistance request includes location data of the second device.

17. A computer program product as recited in claim 11, comprising program code executable by the device to cause the device to receive an alert, wherein a type of the alert is an emergency assistance request.

18. A computer program product as recited in claim 11, wherein the access credential is a staff-specific known security question.

19. A computer program product as recited in claim 11, comprising program code executable by the device to cause the device to receive location data of at least one patient every predetermined amount of time; and update a display, on the device, with the received location data.

20. A system configured for performing a patient wellness check, the system comprising:

the computer program product as recited in claim 11; and
a controller for executing the program code.

* * * * *